United States Patent
Shirahase et al.

(10) Patent No.: US 6,242,208 B1
(45) Date of Patent: Jun. 5, 2001

(54) $LDH_1$ ASSAY

(75) Inventors: Yasushi Shirahase; Kenji Isshiki; Yoshifumi Watazu, all of Hyogo (JP)

(73) Assignee: International Reagents Corporation, Hyogo-ken (JP)

(*) Notice: Subject to any disclaimer, the term of this patent is extended or adjusted under 35 U.S.C. 154(b) by 0 days.

(21) Appl. No.: 08/235,238

(22) Filed: May 2, 1994

Related U.S. Application Data

(63) Continuation of application No. 07/646,999, filed on Jan. 21, 1991, now abandoned, which is a continuation-in-part of application No. 07/375,951, filed on Jul. 6, 1989, now abandoned.

(30) Foreign Application Priority Data

Jul. 15, 1988 (JP) .................................................. 63-177579

(51) Int. Cl.[7] ....................................................... C12Q 1/32
(52) U.S. Cl. .................................................. 435/26; 435/24
(58) Field of Search ...................... 435/4, 12, 13, 435/23, 24, 26; 436/175, 825; 252/95, 100, 186.1

(56) References Cited

U.S. PATENT DOCUMENTS

| | | | |
|---|---|---|---|
| 4,224,406 | 9/1980 | Gomez et al. | 435/7.4 |
| 4,250,255 | 2/1981 | Sanford | 435/26 X |
| 4,803,159 | 2/1989 | Smith-Lewis | 435/26 |
| 5,158,873 | * 10/1992 | Abbott et al. | 435/26 |

FOREIGN PATENT DOCUMENTS

| | | | |
|---|---|---|---|
| 0292838 | 11/1988 | (EP) | 435/26 |
| 2278997 | 12/1987 | (JP) | 435/26 |
| 9001067 | * 2/1990 | (WO) | 435/26 |
| 9001067 | 8/1990 | (WO) | 435/26 |

OTHER PUBLICATIONS

*Research Disclosure*, vol. 163, Nov. 1977, pp. 63–67, Disclosure No. 16370.*
Patent Abstracts of Japan, vol. 9, No. 309 (Dec. 1985).
Patent Abstracts of Japan, vol. 13, No. 39 (Jan. 1989).
Boyer, P.D., The Enzymes, vol. XI, Part A, pp. 257–258 (1975).
Li., S., S.–L., et al, Eur. J. Biochem, 149, 215–225 (1985).
Selmeci, L., et al, Experimentia 27/8, pp. 888–889, Aug. 15, 1971.
Forman, H.J., et al, The Journal of Biological Chemistry, vol. 252, No. 10, 3379–3381 (1977).
Hoppe–Seyler's Z. Physiol. Chem. Abstract, Jeckel et al, 354, pp. 737–738, Jul. 1973.*
Forman et al, "Effects of Chaotropic Agents versus Detergents . . ." *The Journal of Biological Chemistry*, vol. 252, No. 10 (1977) pp. 3379–3381.*

* cited by examiner

Primary Examiner—Ralph Gitomer

(57) ABSTRACT

By a process comprising inhibiting $LDH_2$, $LDH_3$, $LDH_4$ and $LDH_5$ in a sample with a protease in the presence of a protein-denaturating agent and then determining $LDH_1$ remaining uninhibited, $LDH_1$ in the sample is easily determined.

7 Claims, No Drawings

LDH$_1$ ASSAY

RELATED APPLICATION

This application is a continuation of application Ser. No. 07/646,999, filed Jan. 21, 1991 now abandoned which is in turn a continuation-in-part of Ser. No. 07/375,951 filed Jul. 6, 1989, now abandoned.

BACKGROUND OF THE INVENTION

1. Field of the Invention

The present invention relates to a process for the determination of an LDH$_1$ fraction in a sample.

2. Description of the Related Art

LDH (lactate dehydrogenase) has five isozymes, that is LDH$_1$ through LDH$_5$. Each of organs has its own composition of the isozymes. For example, LDH$_1$ is present in a myocardium in the largest amount. Since LDH$_1$ escapes from the myocardium into blood under a condition of a myocardial infarction, a rise in serum LDR$_1$ level can be diagnostic for such a disease. Therefore, an LDH$_1$ isozyme assay is clinically significant.

In a most common LDH isozyme assay, LDH$_1$, LDH$_2$, LDH$_3$, LDH$_4$ and then LDH$_5$ are fractionated in the order of electrophoretic mobility. An immunological LDH assay is also known. In other LDH assay disclosed in Japanese Patent Publication No. 6477/1983, a coenzyme derivative (e.g. reduced type nicotinamide adenine dinucleotide) is used. In addition, LDH assays wherein a sample is treated under an alkaline condition are described in Japanese Patent Publication No. 28280/1985 and Japanese Patent Kokai Publication No. 278997/1987.

The above-mentioned electrophoretic or immunological assay is unsuitable for clinical autoanalysis because of complicated process and long operation time. In addition, the LDH isozymes may be insufficiently fractionated by the electrophoretic method.

Strictly speaking, it is impossible to assay the LDH isozyme fractions by the method wherein the coenzyme derivative is used, while the ratio of H subunit to M subunit in the enzyme can be suitably determined by the method.

In the method comprising the alkaline treatment of the sample, more than 50% of LDH$_1$ may be inactivated during the inhibition of the other isozymes. In addition, the process is complicated and takes a long time.

Thus, the above-mentioned conventional LDH assays are unsatisfactory for a clinical examination.

SUMMARY OF THE INVENTION

An object of the present invention is to provide an LDH$_1$ assay useful for the clinical examinations including autoanalysis.

Accordingly, the present invention provides a process for the determination of an LDH$_1$ fraction in a sample, which comprises inhibiting LDH$_2$, LDH$_3$, LDH$_4$ and LDH$_5$ in the sample with a protease in the presence of a protein-denaturating agent and then determining LDH$_1$ remaining uninhibited.

DETAILED DESCRIPTION OF THE INVENTION

The present process is suitable for the determination of the LDH$_1$ fraction in a clinical sample such as serum or plasma.

The protease used in the present invention may be any protease suitable for the purpose of the invention. Specific examples of the protease are serine proteases (e.g. trypsin, α-chymotrypsin, subtilisin, proteases K, etc.), cystein proteases (e.g. papain, bromelain, clostripain, poliovirus protease, etc.), carboxy proteases (e.g. pepsin, etc.), metalloproteases (e.g. thermolysin, collagenase, dispase, etc.), thrombin, elastase, endoprotease, carboxypeptidase, pronase, and cathepsin. They may be used independently or as a mixture to two or more of them. Proteases disclosed in Japanese Patent Kokai Publication No. 149399/1985 may also be used.

Although the amount of the protease is not critical in the present invention and varies with other assay conditions, α-chymotrypsin, for example, can be used in a concentration in the range of from 10 to 1,000 units/ml.

In the present invention, any protein-denaturating agent having an activity suitable for the process can be used. Specific examples of the protein-denaturating agent are bile acids (e.g. cholic acid, deoxycholic acid, taurocholic acid, taurodeoxycholic acid, etc.), guanidine derivatives (e.g. guanidine hydrochloride, guanidine sulfate, guanidine nitrate, guanidine thiocyanate, etc.), urea compounds (e.g. urea, thiourea, etc.), thiocyanate, trichloroacetic acid or its salts, perchloric acid or its salts, anionic surfactants (e.g. N-lauroyl sarcosinate, sodium dodecylsulfate, etc.), cationic surfactants (e.g. dodecyltrimethylammonium, dodecylamine hydrochloride, etc.) and mixtures thereof.

Although the amount of the protein-denaturating agent is not critical and varies with other assay conditions, for example 0.05 to 5 M guanidine can be used.

The LDH$_1$ isozyme remaining uninhibited can be determined according to an enzyme assay selected from a lot of conventional assays widely used in clinical examinations. Such an assay used in the present process should be easily carried out within a short time with high precision, sensitivity and accuracy.

In a preferred embodiment of the present process, the LDH$_1$ isozyme remaining uninhibited is determined by an enzyme assay which comprises catalytically developing a chromogen or dye precursor with the isozyme and then measuring absorption in a visible light range. It is also possible to measure ultraviolet absorption of coenzyme NADH reduced by a catalytic effect of the LDH$_1$ isozyme.

In another preferred embodiment, the LDH$_1$ isozyme is determined according to the Wroblewski method which is a well-known enzyme assay performed under a neutral condition. It is found that the inhibition of the isozymes LDH$_{2-5}$ can be effected in a wide pH range according to the present invention (cf. Example 1). Therefore, when the determination of the LDH$_1$ isozyme remaining uninhibited is performed under a neutral condition, the present assay can be advantageously carried out under the same neutral condition throughout the assay, while complicated pH correction is necessary in the above-mentioned conventional assay comprising the alkaline treatment of the sample.

PREFERRED EMBODIMENTS OF THE INVENTION

The present invention is further illustrated by the following Examples. However, the invention is not restricted by the Examples.

EXAMPLE 1

To an authentic sample (0.04 ml) of each of the isozymes LDH$_{1-5}$, which was obtained by purifying human blood, a buffer (0.2 ml) containing α-chymotrypsin (450 units/ml)

and 0.65 M guanidine was added and incubated at 37° C. for 5 minutes. The buffers used and pH values thereof were as shown in the following Table 1.

Then, after the addition of a 0.1 M Tris buffer (2.5 ml) containing 2 mM sodium pyruvate and 0.2 mM NADH, by which the pH value was regulated at 7.8, a changing rate of absorbance per minute was measured at 340 nm. Residual activity of each isozyme was calculated from the measured value. The results are shown in the following Table 1.

It was found that only the $LDH_1$ fraction among the isozymes $LDH_{1-5}$ could be determined by the present assay and that the $LDH_1$ isozyme remained uninhibited at any pH value during the inhibition of the other isozymes.

Therefore, when the $LDH_1$ isozyme remaining uninhibited is determined under a neutral condition, the present assay can be advantageously carried out in a pH range between 6 and 8, in particular under a neutral condition throughout the assay without complicated pH correction.

TABLE 1

| pH (Buffer) | Residual activity (%) of | | | | |
|---|---|---|---|---|---|
| | $LDH_1$ | $LHD_2$ | $LDH_3$ | $LDH_4$ | $LDH_5$ |
| 6 (MES) | 83 | 1 | 1 | 0 | 0 |
| 7 (PIPES) | 85 | 2 | 0 | 1 | 0 |
| 8 (Tris) | 83 | 2 | 1 | 0 | 0 |
| 9 (CHES) | 80 | 1 | 0 | 0 | 0 |
| 10 (CHES) | 74 | 1 | 0 | 0 | 0 |
| 11 (CAPS) | 69 | 0 | 0 | 0 | 0 |

Notes:
MES: 2-(N-Morpholino)ethanesulfonic aicd monohydrate.
PIPES: Piperazine-N,N'-bis(2-ethanesulfonic acid).
Tris: Tris(hydroxymethyl)aminomethane.
CHES: 2-(Cyclohexylamino)ethanesulfonic acid.
CAPS: 3-Cyclohexylaminopropanesulfonic acid.

EXAMPLE 2

To the same sample (0.04 ml) as used in Example 1, a 0.1 M Tris buffer (pH 7.8; 0.2 ml) containing subtilisin (5 units/ml) and sodium deoxycholate (1.5%) was added and incubated at 37° C. for 5 minutes. Then, after the addition of a 0.1 M Tris buffer (pH 7.8; 2.5 ml) containing 2 mM sodium pyruvate and 0.2 mM NADH, the residual activity of each isozyme was determined in the same way as in Example 1. The results are shown in Table 2.

It was found that the present $LDH_1$ assay could be effectively carried out at pH 7.8.

TABLE 2

| Residual activity (%) of | | | | |
|---|---|---|---|---|
| $LDH_1$ | $LDH_2$ | $LDH_3$ | $LDH_4$ | $LDH_5$ |
| 83 | 0 | 0 | 0 | 0 |

EXAMPLE 3

As the sample, 15 human sera (each 0.04 ml) were used. Total LDH activity of each sample was known as shown in the following Table 3.

In the same way as in Example 1, a changing rate of absorbance per minute was measured. Then, the $LDH_1$ activity shown in the Table 3 was determined with using a calibration curve.

Separately, the sera were subjected to a conventional immunological assay of the $LDH_1$ isozyme (with using ISOMUNE-LD (trademark); Roche). The results are also shown in the Table 3.

The results of the present process well corresponded with those of the conventional immunological assay.

TABLE 3

| | Total LDH | $LDH_1$ activity (unit/1) determined by | |
|---|---|---|---|
| Sample | activity (units/1) | the present process | the conventional immunological assay |
| 1 | 386 | 84 | 87 |
| 2 | 290 | 85 | 89 |
| 3 | 305 | 89 | 94 |
| 4 | 242 | 45 | 44 |
| 5 | 342 | 113 | 118 |
| 6 | 2147 | 1113 | 1138 |
| 7 | 239 | 73 | 69 |
| 8 | 623 | 181 | 181 |
| 9 | 387 | 70 | 74 |
| 10 | 423 | 113 | 109 |
| 11 | 1812 | 500 | 483 |
| 12 | 322 | 79 | 73 |
| 13 | 906 | 247 | 262 |
| 14 | 485 | 117 | 115 |
| 15 | 1011 | 288 | 287 |

EXAMPLE 4

To the same sample (10 μl) as used in Example 1, a 50 mM MES buffer (pH 6.0; 75 μl) containing 0.5 M guanidine hydrochloride, 2% TRITON (trademark) X-405 and a protease shown in the following Table 4 was added. After incubating at 37° C. for 5 minutes, a 0.1 M Tris buffer (pH 8.0; 400 μl) containing 2 mm sodium pyruvate and 0.2 mM NADH was added. Then, the residual activity of each isozyme was determined in the same way as in Example 1. The results are shown in the Table 4.

It was found that $LDH_1$ fraction could be determined with using any protease, preferably with using carboxypeptidase Y, cathepsin C or α-chymotrypsin.

TABLE 4

| | Residual activity (%) of | | | | |
|---|---|---|---|---|---|
| | $LDH_1$ | $LDH_2$ | $LDH_3$ | $LDH_4$ | $LDH_5$ |
| Pepsin | 41 | 22 | 5 | 0 | 0 |
| Carboxypeptidase P | 96 | 63 | 60 | 60 | 6 |
| Carboxypeptidase Y | 100 | 1 | 0 | 0 | 0 |
| Cathepsin | 80 | 2 | 1 | 1 | 1 |
| α-Chymotrypsin | 99 | 11 | 2 | 2 | 1 |

EXAMPLE 5

To the same sample (0.04 ml) as used in Example 1, a Tris buffer (pH 8.0; 0.2 ml) containing either α-chymotrypsin (450 units/ml) or 0.65 M guanidine was added and incubated at 37° C. for 5 minutes. Then, after the addition of a 0.1 M Tris buffer (2.5 ml) containing 2 mM sodium pyruvate and 0.2 mM NADH, by which pH value was regulated at 7.8, the residual activity of each isozyme was determined in the same way as in Example 1. The results are shown in Table 5.

It was found that the $LDH_{2-5}$ fractions were insufficiently inactivated. Therefore, it is essential in the present assay to use a protease in the presence of the protein-denaturating agent.

TABLE 5

| | Residual activity (%) of | | | | |
| --- | --- | --- | --- | --- | --- |
| | LDH$_1$ | LDH$_2$ | LDH$_3$ | LDH$_4$ | LDH$_5$ |
| When guanidine was added without α-chymotrypsin | 96 | 87 | 79 | 45 | 40 |
| When α-chymotrypsin was added without guanidine | 100 | 78 | 29 | 2 | 0 |

What is claimed is:

1. A process for the determination of LDH$_1$ in a sample selected from the group consisting of human serum and human plasma, which comprises inhibiting LDH$_2$, LDH$_3$, LDH$_4$ and LDH$_5$ in the sample with α-chymotrypsin in the presence of a protein-denaturating agent and then determining LDH$_1$ remaining uninhibited, wherein the LDH$_1$ remaining uninhibited is determined according to a total LDH isozyme assay which comprises catalytically developing a chromogen or dye precursor with the LDH isozyme remaining uninhibited and then measuring absorption in a visible light range or comprises measuring ultraviolet absorption of coenzyme NADH reduced by catalytic effect of the LDH isozyme remaining uninhibited.

2. The process of claim 1, wherein said inhibiting comprises adding α-chymotrypsin at a concentration in the range of from 10 to 1,000 units/ml, to the sample.

3. The process of claim 1, wherein the protein-denaturating agent is at least one agent selected from the group consisting of cholic acid, deoxycholic acid, taurocholic acid, taurodeoxycholic acid, guanidine hydrochloride, guanidine sulfate, guanidine nitrate, guanidine thiocyanate, urea, thiourea, thiocyanate, trichloroacetic acid and its salts, perchloric acid and its salts, anionic surfactants and cationic surfactants.

4. The process of claim 3, wherein the protein denaturing agent is guanidine and said inhabiting comprises adding 0.05 to 5 M guanidine to the sample.

5. The process of claim 1 wherein the total LDH isozyme assay is carried out at pH 6–8.

6. The process of claim 5 wherein the protein denaturing agent is guanidine hydrochloride and said inhibiting comprises adding α-chymotrypsin at a concentration of 400–1000 units/ml to the sample and adding 0.5–0.7 M guanidine hydrochloride to the sample.

7. The process of claim 1 wherein the protein-denaturating agent is guanidine hydrochloride.

* * * * *